United States Patent [19]

Needleman

[11] Patent Number: 4,557,864
[45] Date of Patent: Dec. 10, 1985

[54] ATRIAL PEPTIDES

[75] Inventor: Philip Needleman, Olivette, Mo.

[73] Assignee: Washington University, St. Louis, Mo.

[21] Appl. No.: 634,858

[22] Filed: Jul. 26, 1984

Related U.S. Application Data

[60] Division of Ser. No. 569,684, Jan. 10, 1984, Pat. No. 4,496,544, and a continuation-in-part of Ser. No. 551,372, Nov. 10, 1983, abandoned.

[51] Int. Cl.$^4$ ............................................. C07C 103/52
[52] U.S. Cl. ............................................. 260/112.5 R
[58] Field of Search .................. 424/177; 260/112.5 R

[56]  References Cited

PUBLICATIONS

DeBold, J. Histochem. Cytochem., 26, 1094-1102 (1978).
DeBold, Life. Sci., 89-94 (1981).
Trippodo, Proc. Soc. Exp. Biol. Med., 170, 502-508 (1982).
DeBold, Fed. Proc., 46(3) Abst. 1870, p. 611 (1983).
Grammer, Biochem. Biophys. Res. Commun., 116(2), 696-703 (1983).
Currie, Science, 221, 71-73 (1983).
Needleman, Fed. Proc., 42(3), Abst. 1872, p. 612 (1983).
Currie, Science, 223, 67-69 (1984).
Flynn, Biochem. Biophys. Res. Commun., 117(3) 859-65 (1983).
Thibault, FEBS Letters, 164, 286-90 (1983).
Deth et al., Fed. Proc., 41(4) 983, Abst. 4170, (1982).
Chem. Abstr., vol. 94, (1981) 62919f.
Science (1983) vol. 221, 74-73.
Chem. Abstr., vol. 97, (1982) 175913e.
Science (1983) 67-69.
FEBS, 1268, vol. 167 (1984) 352-357.
Biochem. and Biophys. Res. Commun., vol. 118, (1984) 131-139.
Biochem. and Biophys. Res. Commun., vol. 119, (1984) 524-529.
Biochem. and Biophys. Res. Commun., vol. 117, 859-865 (1983).

*Primary Examiner*—Delbert R. Phillips
*Attorney, Agent, or Firm*—Scott J. Meyer; James W. Williams, Jr.

[57]  ABSTRACT

Novel atrial peptides having useful natriuretic activity are disclosed with the following amino acid sequence:

$$R_1\text{-cys-phe-gly-gly-arg-ile-asp-arg-ile-gly-ala-gln-ser-gly-leu-gly-cys-asn-}R_2$$

wherein
 $R_1$ = H, ser, ser-ser, and
 $R_2$ = OH, ser, ser-phe-arg, ser-phe-arg-tyr, or the physiologically acceptable salts, esters or amides thereof.

1 Claim, 2 Drawing Figures

ATRIAL PEPTIDES

CROSS-REFERENCE TO RELATED APPLICATION

This is a division of application Ser. No. 569,684, filed Jan. 10, 1984, now U.S. Pat. No. 4,496,544 issued Jan. 29, 1985, and a continuation-in-part of copending application Ser. No. 551,372, filed Nov. 10, 1983, abandoned.

BACKGROUND OF THE INVENTION

This invention relates to novel atrial peptides having useful natriuretic activity.

It is known that the cells of the atrial myocardium in mammals contain numerous membrane-bound storage granules. These characteristic secretory granules, which have been observed in the rat, dog, cat and human atria, resemble those which are in peptide-hormonal producing cells. See DeBold et al., *J. Histochem. Cytochem.* 26, 1094–1102 (1978). It has been reported that crude tissue extracts of atrial myocardium when injected intravenously into non-diuretic rats produced a rapid and potent natriuretic response. See DeBold et al., *Life Sciences* 28, 89–94 (1981). Partial purification of rat atrial homogenates with a brief boiling step and fractionation on Sephadex ® was achieved by Trippodo et al., *Proc. Soc. Exp. Biol. Med.* 170, 502–508 (1982). Natriuretic activity was found by these investigators in the overall molecular weight range of 3600 to 44,000 daltons and in peptide fractions of both the higher molecular weight range of 36,000–44,000 daltons and a lower molecular weight range of 3600–5500 daltons.

In a more recent publication, DeBold et al., *Fed. Proc.* 42(3), Abstract 1870, page 611 (1983), report the purification of an atrial natriuretic peptide having a molecular weight of 5150 daltons and a sequence of 47 amino acids which the investigators designated "Cardionatrin I". Three additional peaks with natriuretic activity were obtained by high performance liquid chromatography (HPLC) procedures.

In a still later publication, Grammer et al., *Biochem. Biophys Res. Commun.* 116(2), 696–703, Oct. 31, 1983, disclose the partial purification of a rat atrial natriuretic factor having a molecular weight of approximately 3800 and containing 36 amino acid residues.

Rat atrial extracts also have been fractionated into low molecular weight fractions (<10,000 daltons) and high molecular weight fractions (20,000–30,000 daltons) both of which in vitro relaxed smooth muscle and were potent natriuretic agents when administered intravenously to rats. See Currie et al., *Science* 221, 71–73 (1983).

BRIEF DESCRIPTION OF THE INVENTION

In accordance with the present invention, novel peptides are provided which exhibit useful natriuretic activity. These biologically active peptides have the following amino acid sequence:

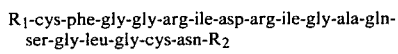

$R_1$-cys-phe-gly-gly-arg-ile-asp-arg-ile-gly-ala-gln-ser-gly-leu-gly-cys-asn-$R_2$ wherein $R_1$ = H, ser, ser-ser, and $R_2$ = OH, ser, ser-phe-arg, ser-phe-arg-tyr, or the physiologically acceptable salts, esters or amides thereof.

In the peptide structure, the amino acid components are designated by conventional abbreviations as follows:

| Amino Acid | Abbreviated Designation |
| --- | --- |
| L-Alanine | ala |
| L-Arginine | arg |
| L-Asparagine | asn |
| L-Cysteine | cys |
| L-Glutamine | gln |
| Glycine | gly |
| L-Isoleucine | ile |
| L-Leucine | leu |
| L-Methionine | met |
| L-Phenylalanine | phe |
| L-Proline | pro |
| L-Serine | ser |
| L-Tyrosine | tyr |

The peptide materials of this invention have been isolated in a highly purified form which did not exist in the rat myocardium from which they were initially obtained. That is, they have been prepared in a form which is essentially free of other peptides, and free from other cellular components and tissue matter. These new atrial peptides exhibit physiological characteristics which suggest that they are important to medical science in the study of the endocrine system of the cardiac atria with respect to humoral agents for modulation of extracellular volume, sodium and vascular resistance.

In particular, the novel peptides of this invention have indicated therapeutic use as a diuretic, natriuretic, renal vasodilator and smooth muscle relaxant. That is, they exert profound effects on sodium, urine volume, renal vasodilation and smooth muscle tone.

In brief, these novel peptides have been obtained by fractionation of rat atrial extracts by gel filtration chromatography to provide a high and a low molecular weight fraction, both of which had useful natriuretic activity. The lower molecular weight peak was resolved by ion-exchange chromatography into two peaks which possessed natriuretic activity and which either preferentially relaxed only the intestinal (chick rectum) muscle strips or which relaxes both vascular (rabbit aorta) and intestinal smooth muscle preparations. The intestinal smooth muscle relaxant was separated into 4 peaks and purified to homogenity by reversed phase high performance liquid chromatography (HPLC). Sequence analysis established the structure of this serine-, glycine-rich peptide and demonstrated that the four biologically active peptides differed from each other by the lack of the first and the second amino terminal serine residues or of the C-terminal serine residue, respectively. The 21 amino acid peptide was designated atriopeptin I, and the other three peaks which relaxed intestinal strips and were natriuretic and diuretic, but which were ineffective on blood vessel strips, were designated des-ser[1]-atriopeptin I, des-ser[1], ser[2]-atriopeptin I and des-ser[21]-atriopeptin I, respectively.

Similarly, the vascular smooth muscle relaxant which was the more potent natriuretic-diuretic compound was resolved into two major peaks on HPLC. Surprisingly, the amino terminal 21 amino acids of both rabbit aorta relaxants was homogeneous with that of the intestinal relaxant but the 23 amino acid peptide (designated atriopeptin II) possessed a phe-arg, and the 24 amino acid peptide (designated atriopeptin III) was extended by a phe-arg-tyr at the carboxy terminus. This family of closely related peptides is believed to be derived from a similar high molecular weight precursor and the biological selectivity and potency of the smaller peptides may be determined by the action of a limited sequential proteolytic cleavage.

The shorter 21 amino acid peptide (designated atriopeptin I) relaxes intestinal but not vascular smooth muscle and is natriuretic and diuretic in vivo. The second peptide (atriopeptin II) contained 23 amino acids, i.e. the same 21 amino acids with a C-terminal phe-arg extension which results in an agent that relaxes both vascular and intestinal smooth muscle as well as being a potent natriuretic-diuretic in vivo.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in connection with the accompanying drawings in which:

Figure 1:
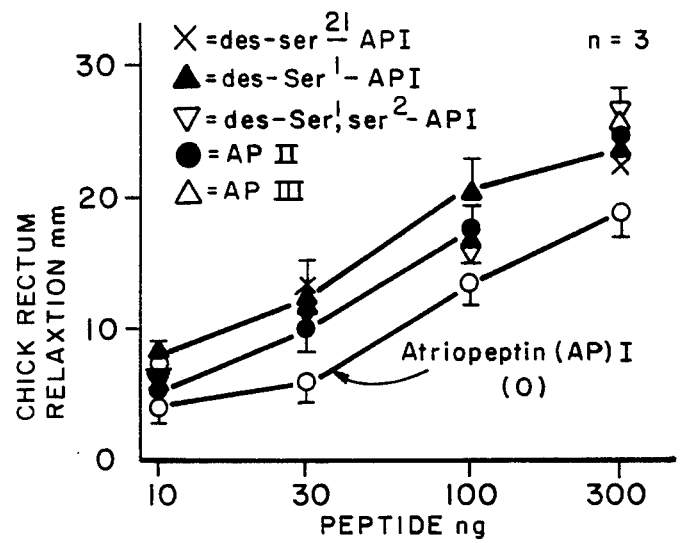
FIG. 1 is a graphical representation which shows the comparative intestinal smooth muscle relaxant activity (chick rectum relaxation in mm) of the novel atrial pepetides in one embodiment of the invention.

The initial source material for isolating the peptides of this invention was the frozen rat heart. Over 2500 such rat hearts were subjected to a sequence of steps for the isolation of the desired peptides. The steps for isolation can be briefly described as:

(a) Preparing a crude homogenate of mammalian atrial tissue and centrifuging;
(b) Boiling the supernatant and centrifuging;
(c) Desalting the supernatant by gel filtration chromatography on Sephadex ® G-15 resin;
(d) Gel filtration chromatography of the protein fraction on Sephadex ® G-75 resin;
(e) Ion exchange chromatography of the low molecular weight protein fraction on SP-Sephadex ® C-25 resin;
(f) High performance liquid chromatography (HPLC) of the two main protein fractions; and;
(g) Recovering the separated atrial peptide fractions.

The aforesaid Sephadex chromatography resins are well-known materials available from Pharmacia Fine Chemicals, Piscataway, NJ.

Bioassays of the isolated peptides were made on rabbit aorta strips and on segments of chick rectum under physiologically acceptable conditions. Rabbit aorta strips maintained in tone by a continuous infusion of norepinephrine constituted a reliable and sensitive assay tissue. Use of an isolated carbachol (a muscarinic agent) contracted chick rectum preparation, however, provided a more rapid and simpler assay that facilitated the testing of a larger number of samples.

Natriuretic activity of the isolated peptides was determined by injection intravenously in rats and determining the effect on fractional sodium excretion in the urine.

These methods of determining biological activity (smooth muscle relaxant and natriuresis) as developed by a research group led by the inventor are further described by Currie et al., Science 221, 71–73 (1983).

The following detailed Examples will further illustrate the invention although it will be understood that the invention is not limited to these specific Examples. In the Examples, CRF means chick rectum factor while RAF means rabbit aorta factor.

EXAMPLE 1

Methods

Relaxation of smooth muscle in vitro

Bioassay. Spiral strips of rabbit thoracic aorta and segments of chick rectum under 1 gm tension were continuously perfused at 10 ml/min with oxygenated Krebs-Henseleit solution (37°). Resting tone was induced by either $2 \times 10^{-8}$M norepinephrine (aorta) or $2 \times 10^{-8}$M carbachol (rectum). The effects of test substances then were determined by application with micropipets to the stream of medium flowing over the tissues, using as standards nitroglycerin (aorta) and isoproterenol (rectum). Column fractions were freeze dried and residues dissolved in phosphate buffered saline for bioassay.

Natriuresis. The natriuretic activity of extracts was determined in 250–300 gm male Sprague-Dawley rats under dial-urethane anesthesia. A suprapubic silastic bladder catheter was placed for urine collection and a tail vein catheter was used for infusion of 0.225% NaCl in 5% dextrose solution at 38 $\mu$l/min. After an equilibration period of one hour, two 10 minute (min) baseline urine collections were followed by rapid intravenous injection of the test substance and 3 more ten min urine collections completed. Following a one hour re-equilibration period, a second set of collections with a second injection of the test substances was completed. Urine volume was determined by weighing in tared containers. Sodium concentration was measured by flame photometry.

Preparation and purification of chick rectum factor (CRF) and rabbit aorta factor (RAF). Homogenates were prepared from frozen atrial tissue in ~30 g lots derived from 200 rats by dispersion in 10 vol/wt tissue of phosphate buffered saline in a 1 quart Waring blender (1 min) followed by Polytron PT20ST (20 seconds) at maximum speed. Suspensions were centrifuged 10 min at $200 \times$ g. After heat treatment (10 ml aliquots in $18 \times 150$ mm test tubes immersed 10 min in a boiling water bath) this supernatant was centrifuged again at $12000 \times$ g for 10 min. Acetic acid (glacial) then was added to the supernatant fluid to 0.5M, and the resultant suspension clarified by a final centrifugation ($27000 \times$ g for 15 min). The supernatant was chromatographed on a G-15 Sephadex column ($8 \times 36$ cm) in 0.5M acetic acid at 600 ml/hr and the protein fraction was concentrated by freeze drying. The combined material derived from 600 rats then was dissolved in 0.5M acetic acid and supplied to a $5 \times 90$ cm G-75 Sephadex column, eluting with 0.5M acetic acid at 96 ml/hr. Biological activity (smooth muscle relaxant and natriuresis) was found by assay methodology previously described by Currie et al., Science 221, 71–73 (1983) in two peaks: a high (20,000 to 30,000) and a low (less than 10,000) molecular weight fraction.

Further purification of the low molecular weight fraction was achieved by ion exchange chromatography. The combined material from 1200 rats was applied to a column of SP-Sephadex C-25 (20 gm, dry weight, forming a 5×7 cm column) in a 25 mM ammonium acetate/500 mM acetic acid. The chromatogram was developed by application of a linear gradient of ammonium acetate increasing at 23.4 mM/hr at a flow rate of 96 ml/hr, with the acetic acid held at 500 mM. Biological activity was found only in two main fractions: one, designated peak CRF (eluted at 150 mM ammonium acetate), which contained chick rectum relaxant factor (CRF), and the second, designated peak RAF (at 270 mM ammonium acetate), which contained rabbit aorta relaxant factor (RAF). Both fractions were enriched in natriuretic activity as well.

The final stage of purification was accomplished by HPLC with UV monitoring at 215 nm. The CRF and RAF fractions from the SP-Sephadex column were lyophilized repeatedly to remove volatile materials, redissolved in 0.1% trifluoroacetic acid, and then HPLC was run on a Brownlee RP-300 Aquopore Column (4.6 mm×25 cm) using the following gradients at 1.0 ml/min. CRF: 0→10%A over 3.8 min then 10%A→14.8%A over 60 min then 14.8%A→16.4%A over 100 minutes. Three peaks of CRF activity eluted at 113.8 min. RAF: 0→16%A over 3.6 min then 16%A→22.4%A over 80 minutes. A band of RAF activity eluted at 48.8 min. In all cases solvent A=0.1% trifluoracetic acid/acetonitrile, B=0.1% trifluoroacetic acid/$H_2O$. The bioactive fractions were reinjected on a Vydac column ($C_{18}$, 300 Å pore size, 4.6 mm×25 cm) acid eluted at 1.0 ml/min using a gradient of 0→50%C over 50 min. The CRF sample resolved into one major peak (CRF I, 29.3 min) and two minor peaks (CRF-II and -III, 29.5, 29.7 min). The RAF sample provided a major peak (RAF-I, 31.0 min) and a minor peak RAF-II, 31.5 min). Products were lyophilized and when stored at −20°, exhibited good stability.

Edman degradation. The above-isolated polypeptides were sequentially degraded utilizing an Applied Biosystems Model 470A gas phase sequencer as described by Hunkapiller et al., *Methods in Enzymol.* 91 (1), Chapter 36, Academic Press, N.Y., 1983. Several modifications included the omission of benzene as one of the solvents employed, and the replacement of methanol with acetonitrile as solvent 4 in the system. In addition, the conversion reagent utilized (reagent 4) was 25% trifluoracetic acid (in $H_2O$ v/v). Coupling times were reduced to about 600 sec total, while cleavage times remained at 850 sec. Thirty or more cycles were completed in each run with one degradation each for CRF (665 pmoles output yield), reduced/alkylated CRF (600 pmoles), and RAF (1178 pmoles). Phenylthiohydantoin amino acids were identified using high performance liquid chromatography as adapted from Hunkapiler and Hood, *Methods in Enzymol.* 91 (1), Chapter 43, Academic Press, N.Y., 1983. Average repetitive yield values of 91% were determined for those amino acid derivatives deemed worthy of accurate quantitation.

The method described, above, provides the sequence of steps followed in the purification of 1,200 rat hearts. In order to assign a relative biological activity, the relaxant activity of the atrial extracts was compared to a nitroglycerin standard curve on the blood vessel (rabbit aorta) strips and to isoproterenol on the intestinal (chick rectum) strips. The initial crude homogenate of rat atria was too contaminated to determine total activity. The 10 min. boiling step facilitated the purification by eliminating a great deal of protein prior to desalting on the Sephadex G-15 column. The low molecular weight fraction obtained from the gel filtration column was further separated on the ion exchange column based on differences in the preferential spasmolytic activity of the various fractions. Thus, testing a 10 μl aliquot of each fraction demonstrated the presence of two peptides, one of which preferentially relaxed the intestinal smooth muscle and one which at low dose preferentially relaxed the blood vessel strip. However, a complete dose-response analysis of both peaks indicated that chick rectum relaxant exhibited a pronounced selectivity such that even high dose of this peptide was impotent as a blood vessel relaxant. On the other hand, the second peak produced concentration dependent relaxation of both the intestinal and vascular strips. The peak with the preferential selectivity, i.e. the chick rectum relaxant, which also possessed the natriuretic-diuretic activity in vivo, was further investigated as described herein.

The lyophilized chick rectum active factor (CRF) obtained from the SP Sephadex column was fractionated by reversed phase (Brownlee $C_{18}$) HPLC. The CRF was separated into three major fractions (I–III). Each fraction was lyophilized and rechromatographed by HPLC on a VYDAC column ($C_{18}$, 300 Å pore size). There was thus obtained 60 μg protein of CRF-I, 25 μg of CRF-II, and 25 μg of CRF-III. CRF-I was quantitated as a smooth muscle relaxant and produced a concentration dependent relaxation but did not relax the precontracted aorta strips. Intravenous administration of CRF-1 protein produces an increase in urinay sodium concentration.

The purified CRF-I sample was analyzed by gas phase sequencing. The sequences of the closely related low molecular weight spasmolytic/natriuretic peptides as determined in this Example 1 are shown in Table 1, below. The peptides exhibit a large number of serine and glycine residues. The CRF-II and CRF-III merely lack the amino terminal one or two serines present in CRF-I, thereby suggesting that they are amino peptidase cleavage products. The intestinal receptor recognition appears to be tolerant of losses on the amino terminus since CRF-II and III are fully biologically active.

The purified low molecular weight peptide designated RAF-I which exhibited a preferential relaxation of vascular smooth muscle was further analyzed with the gas phase sequentator. Surprisingly, the sequence of the initial 21 amino acids of RAF-I are exactly the same as those observed for CRF-I. The major difference in the peptides resides in the carboxyl terminus. RAF-I is a potent vascular smooth muscle relaxant in vitro and a selective renal vasodilator in vivo. RAF-I also appears to be considerably more potent as a natriuretic substance than CRF-I. The latter peptide requires large doses and produces a variable in vivo response.

TABLE 1

| Amino Acid Sequences |
|---|
| CRF-I: |
| Ser-ser-cys-phe-gly-gly-arg-ile-asp-arg-ile-gly-ala-gln-ser-gly-leu-gly-cys-asn-ser |
| CRF-II: |
| des-ser[1] - CRF-I |
| CRF-III: |
| des-ser[1], ser[2] - CRF-I |
| RAF-I: |
| Ser-ser-cys-phe-gly-gly-arg-ile-asp-arg-ile-gly-ala-gln-ser-gly-leu-gly-cys-asn-ser[21]-phe-arg[23] |

RAF-I and CRF-I can readily be differentiated by charge (on ion exchange chromatography) and mobility on reversed phase HPLC. The carboxy-terminal sequence of the peptides dictates their biological specificity. The shortened carboxy terminus on CRF-I restricts its biological activity to relaxation of the intestinal smooth muscle and weak natriuretic activity. This peptide does not relax isolated blood vessel strips nor does it reduce renal resistance in vivo. On the other hand, the extended carboxy terminal in RAF-I includes the structural features required for vascular receptor recognition and for the initiation of natriuresis and diuresis. The homogeneous nature of amino terminal 21 amino acids in CRF and RAF strongly indicate that they may be derived from the same precursor peptide. Aminopeptidase cleavage of at least the initial two serine residues does not radically compromise biological activity. However, the site of attack on the carboxy portion of the atrial peptide appears to dictate the ultimate biological response. The proteolytic enzyme provides an ideal site for the regulation of the physiological actions of these spasmolytic (natriuretic) peptides.

EXAMPLE 2

Materials and Methods

Purification Scheme

Fourteen hundred frozen rat atria (Biotrol, Indianapolis, IN) were trimmed of extraneous tissue (153 gm wet wt), homogenized in 10 volumes of phosphate buffered saline in the presence of phenylmethylsulfonyl fluoride (1 μ/ml, Sigma Chemical Company, St. Louis, MO) and centrifuged at 2500×g for 10 min. The supernatant was divided into 10 ml aliquots and immersed in a 100° bath for 10 min and centrifuged at 10,000×g for 10 min at 4°. The supernatant was adjusted to 0.5M acetic acid and applied to a Sephadex G-15 column (8×36 cm) and eluted with 0.5M acetic acid (600 ml/hr). The column effluent was lyophilized and reconstituted in 0.5M acetic acid, applied to a Sephadex G-75 column (5×90 cm) and eluted with 0.5M acetic acid at 96 ml/hr. The lyophilized low molecular weight fraction from the G-75 column was applied to SP-Sephadex C-25 (20 g gel, 5×7 cm column) in 25 mM ammonium acetate/0.5M acetic acid and eluted with a linear gradient of ammonium acetate (23.4 mM/hr at 96 ml/hr) in 0.5M acetic acid. Two biologically active fractions eluted at 160 mM which relaxed intestinal but not vascular smooth muscle strips and the other at 270 mM relaxed both vascular and intestinal assay strips. Following lyophilization the low molecular weight peaks were individually purified by reversed phase high pressure liquid chromatography on a Brownlee RP-300 aquapore column (4.6 mm×25 cm) using a mixture of solvent A (0.1% trifluoracetic acid/acetonitrile) and B (0.1% trifluoracetic acid/water) at 1.0 ml/min.

The fraction that eluted from the SP-sephadex column at 160 mM ammonium acetate was run at 0 to 10% A over 3.8 min; then 10 to 14.8% A over 60 min; then 14.8 to 16.4% A over 100 minutes. Atriopeptin I eluted at 15.6% A, des-ser[1]-atriopeptin I eluted at 15.7% A, des-ser[1], ser[2]-atriopeptin I eluted at 15.7% A, and des-ser[21]-atriopeptin I at 15.8% A. The SP-Sephadex fraction that eluted at 270 mM was separated on the same gradient on the HPLC with atriopeptin II being recovered from a gradient 0 to 16% A in 5.8 min and 16 to 22% in 80 min. at 19.6% A, and atriopeptin III at 21.1% A. The bioactive fractions were reapplied to a Vydac octadecasilyl column (300 Å pore size, 4.6 mm×25 cm) and eluted at 1.0 ml/min using a mixture of solvent A (0.05% trifluoroacetic acid in acetonitrile) and B (0.05% trifluoracetic acid in water) employing a gradient 0 to 30% over 30 min. Atriopeptin I appeared at 29.5% A; des-ser[1]-atriopeptin I at 29.7% A; des-ser[1], ser[2]-atriopeptin I at 29.7% A; des-ser[21]-atriopeptin I at 29.9%A; atriopeptin II at 31.5% A; and atriopeptin III at 32% A from a gradient of 10 to 35% over 25 min. The polypeptides were sequentially degraded, utilizing an applied Biosystem Model 470 A gas phase sequencer as described in Example 1. Thirty or more cycles were completed in each run with one degradation each for: the reduced and alkylated atriopeptin I (600 pmoles output yield); des-ser[1]-atriopeptin I (660 pmoles); des-ser[21]-atriopeptin I (520 pmoles); des-ser[1], ser[2]-atriopeptin I (650 pmoles); atriopeptin II (1200 pmoles), and atriopeptin III (850 pmoles). The atriopeptins were reduced and alkylated by dissolving the peptide (0.5–5 nmoles) in 90 μl of 2% SDS (sodium dodecylsulfate) in 0.4M Tris acetate (pH 9.0); 10 μl of 100 mM dithiothreitol was added, flushed with $N_2$, capped and incubated at 37° for 60 min. Then 20 μl of a fresh solution of 120 mM iodoacetamide (which had been recrystallized 3X), flushed with $N_2$, capped and incubated at room temp. for 10 min, then transferred to boiled dialysis tubing and dialyzed against 0.1% SDS for 2 hrs and redialyzed overnight followed by lyophilization. Phenylthiohydantoin amino acids were identified using high performance liquid chromatography as described in Example 1. Average repetitive cycle yields were greater than 90% for each cycle whose signal allowed accurate quantitation. The protein concentration of the purified peptides was determined by the method of Lowry et al., *J. Biol. Chem.* 193, 265–276 (1951). The smooth muscle bioassay technique was performed as described by Currie et al., *Science* 221, 71–73 (1983). Briefly, spiral strips of rabbit thoracic aorta and chick rectum were continuously superperfused at 10 ml/min with oxygenated Krebs-Henseleit medium (37°). In order to detect relaxant substances a resting tone was induced by infusing the vascular smooth muscle preparations with norepinephrine ($2\times 10^{-8}$M.)

The natriuretic-diuretic assay ($U_{Na}V$) percent of the baseline control was performed. The natriuretic-diuretic assay ($U_{Na}V$-percent of baseline control) was performed in 250–300 gm Sprague-Dawley rats anesthetized with 0.4 ml dial-urethane. A suprapubic silastic catheter was placed in the bladder for urine collection and a tail vein catheter was used for infusion of 0.225% NaCl in 5% dextrose at 38 μl/min. After an equilibration period of one hour, two 10 min baseline urine collections were followed by rapid intravenous injection of the test substance and 3 more 10 min urine collections were completed. Urine volume was determined by weighing in tared containers. Sodium concentration was measured by flame photometery.

RESULTS

The purification protocol employed to produce peptides pure enough for sequence analysis is shown in Table 2, below. The initial crude homogenate of rat atria is too contaminated to determine total biological activity. The 10 min boiling step facilitated the purification by eliminating a great deal of protein prior to desalting on the Sephadex G-15 column. The low molecular weight fraction obtained from the gel filtration column was further separated on the ion exchange column based on differences in net charge and in the preferential spasmolytic activity of the various fractions. Thus, the testing of aliquots of each fraction demonstrated the presence of two major peptide fractions, one of which preferentially relaxed the intestinal smooth muscle and one which at low doses relaxed both the blood vessel and the intestinal strip. The lyophilized chick rectum active factor obtained from the SP-Sephadex column was fractionated by reversed phase (Brownlee $C_{18}$) HPLC into four fractions. Similarly, the peak that also possess the vascular relaxation activity was resolved into two main peaks (atriopeptin II and III). Each fraction was lyophilized and rechromatographed by HPLC on a VYDAC column and underwent sequence analysis. The sequences of the closely related low molecular weight spasmolytic/natriuretic peptides as determined in this Example 2 are shown in Table 3, below. The peptides exhibit a large number of serine and glycine residues and contain an internal disulfide ring. The four peptides that selectively act on intestinal but not vascular smooth muscle differ from each other because of the lack at the amino terminal of one or two serine residues, or lack of a C-terminal serine. The peptides that are potent vascular smooth muscle relaxants as well as intestinal spasmolytics contain a carboxyl terminal extension of phe-arg or a phe-arg-tyr in atriopeptin II and III, respectively.

Figure 2:
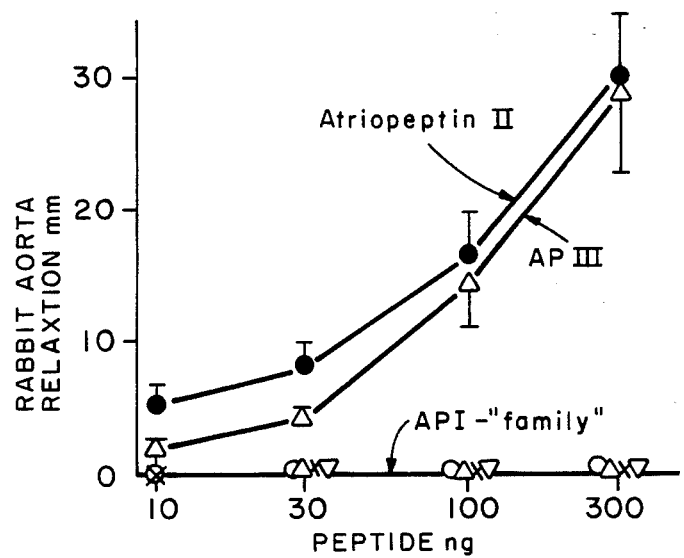
FIG. 2 is a graphical representation which shows the comparative vascular smooth muscle relaxant activity (rabbit aorta relaxation in mm) of the novel atrial peptides in another embodiment of the invention.

A quantitative comparison of the biological activity of the various atrial peptides indicates that intestinal receptor recognition is tolerant of losses on the amino terminus since des-ser$^1$-atriopeptin I and des-ser$^1$, ser$^2$-atriopeptin are active peptides. However, the lack of a phe-arg carboxy extension precludes vaso-relaxant activity and partially reduces in vivo natriuretic-diuretic activity. The in vitro and in vivo potency of atriopeptin II and III are comparable, suggesting that further extension of the C-terminus beyond arg may not further substantially alter activity. FIGS. 1 and 2 illustrate this quantitative comparison of the biological activity of these atrial peptides by the assay methods utilizing the chick rectum and rabbit aorta, respectively, as described hereinbefore.

TABLE 2

|  | Total Protein | Specific Activity μ/mg | Total Activity Units | (Recovery %) |
|---|---|---|---|---|
| Crude Homogenate | 5764 mg | 7.7 | 44,000 |  |
| Boiled Extract | 728 | 154 (1X) | 112,000 | (100%) |
| Sephadex G-15 | 262 | 265 (1.7X) | 69,400 | (62%) |
| Sepahdex G-75 SP-Sephadex C-25: | 17.0 | 2,890 (18.8X) | 49,100 | (44%) |
| Intestinal Relaxant | 1.54 | 11,300 (73.4X) | 17,400 | (16%) |
| Vascular Relaxant HPLC Fractions | 1.20 | 7,620 (49.5X) | 9,140 | (8%) |
| AP-I | 0.114 | 37,600 (244X) | 4,280 | (3.8%) |
| Mixture* | 0.049 | 107,000 (695X) | 5,220 | (4.6%) |
| des-ser$^{21}$-AP I | 0.073 | 62,500 (406X) | 4,550 | (4.1%) |
| AP-II | 0.081 | 52,400 (340X) | 4,260 | (3.8%) |
| AP-III | 0.061 | 62,600 (406X) | 3,810 | (3.3%) |

TABLE 3

ATRIOPEPTIN I

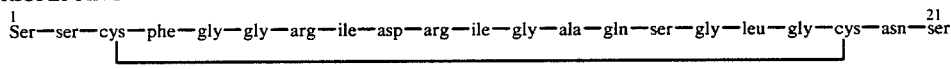

des—ser$^1$—ATRIOPEPTIN I

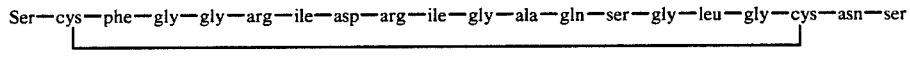

des—ser$^1$, ser$^2$—ATRIOPEPTIN I

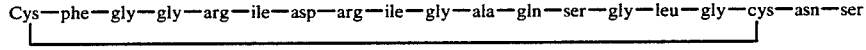

des—ser$^{21}$—ATRIOPEPTIN I

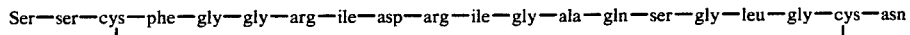

ATRIOPEPTIN II

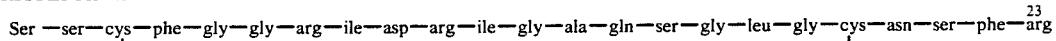

ATRIOPEPTIN III

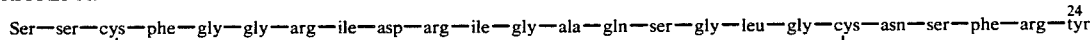

The atrial peptides were tested in vivo in rats for natriuretic potency following intravenous injection of 2 μg of the six peptides. Atriopeptins II and III were equipotent and somewhat more active than atriopeptin I. Further shortening of the 21 amino acid length of the peptide by loss of serines at either the N- or C-terminus resulted in a reduction of the nutriuretic-diuretic potency. The results of this in vivo testing are set forth in Table 4, below.

TABLE 4

| Peptide | Residue No. | n | $U_{Na}V$ | pValue |
|---|---|---|---|---|
| Atriopeptin (AP) I | 1-21 | 7 | 1130 ± 38 | <.05 |
| des-ser$^1$-AP I | 2-21 | 6 | 275 ± 62 | <.05 |
| des-ser$^1$, ser$^2$-AP I | 3-21 |  |  |  |
| des-ser$^{21}$-AP | 1-20 | 8 | 235 ± 70 | NS |
| Atriopeptin II | 1-23 | 3 | 1869 ± 114 | <.005 |
| Atriopeptin III | 1-24 | 6 | 1241 ± 261 | <.01 |

In the isolated perfused rat kidney, atriopeptin II and atriopeptin III produced a concentration dependent renal vasodilation. The peptides which lack the phe-arg C-terminal (i.e., the atriopeptin I family of peptides) were very much less active renal vasodilators.

Various other examples and modifications of the foregoing examples will be apparent to the person skilled in the art after reading the present disclosure without departing from the spirit and scope of the invention, and it is intended that all such examples or modifications be included within the scope of the appended claims. Thus, variations in length and composition of the end groups ($R_1$ or $R_2$) of the peptides or in the individual amino acids of the peptides which do not adversely or detrimentally affect their biologic activity as defined herein are included within the scope of the appended claims.

What is claimed is:

1. A process for preparing a peptide having the amino acid sequence $$R_1\text{-cys-phe-gly-gly-arg-ile-asp-arg-ile-gly-ala-gln-ser-gly-leu-gly-cys-asn-}R_2$$

wherein
  $R_1$ = H, ser, ser-ser, and
  $R_2$ = OH, ser, ser-phe-arg, ser-phe-arg-tyr,
or the physiologically acceptable salts, esters or amides thereof, comprising the steps of:

(a) Preparing a crude homogenate of rat atrial tissue and centrifuging;
(b) Boiling the resulting supernatant for about ten minutes and centrifuging;
(c) Desalting the resulting supernatant by gel filtration chromatography by passing through a column of Sephadex ® G-15 resin and collecting the protein effluent;
(d) Separating the protein effluent into high and low molecular weight protein fractions by gel filtration chromatography by passing through a column of Sephadex ® G-75 resin and collecting the low molecular weight protein fraction;
(e) Separating the low molecular weight fraction into two biologically active protein fractions of preferential spasmolytic activity by ion exchange chromatography by passing through a column of SP-Sephadex ® C-25 resin and collecting the separated low molecular weight fraction which preferentially relaxes intestinal smooth muscle;
(f) Separating the latter low molecular weight fraction into individual peptides of the aforesaid amino acid sequence by subjecting to reversed phase high high performance liquid chromatography on an octadecyl column; and
(g) Recovering any of the separated atrial peptides.

* * * * *

UNITED STATES PATENT AND TRADEMARK OFFICE
CERTIFICATE OF CORRECTION

PATENT NO. : 4,557,864
DATED : December 10, 1985
INVENTOR(S) : PHILIP NEEDLEMAN

It is certified that error appears in the above—identified patent and that said Letters Patent is hereby corrected as shown below:

In the table of Col. 2, line 8 below "L-Asparagine    asn" insert --L-Aspartic Acid    asp--. Below Table 2, col. 10, line 20, insert the following legend: Table 2. Purification of 153 g tissue (atria from 1400 rat hearts). The biological activity was compared on intestinal smooth muscle (chick rectum) strips. Quantitation achieved by performing dose response curves with each peptide in comparison to the response to a standard curve achieved with isoproterenol (the intestinal relaxant). One unit of activity was set to be equivalent to 1 ng of isoproterenol.
  *  Mixture of des-ser$^1$-AP I and des-ser$^1$, ser$^2$-AP I.
  AP = Atriopeptin
  u = Units Below Table 4, col. 10, line 66, insert the following legend: Table 4. Comparative effectiveness of the atrial peptides as natriuretic-diuretic substances _in vivo_. The $U_{Na}V$ data is presented as % of the stable baseline values obtained immediately prior to injection of the peptide. The baseline $U_{Na}V$ was 0.21 ± 0.05 µ equivalents/min.
  *  Mixture of des-ser$^1$-AP I and des-ser$^1$, ser$^2$-AP I.
  NS = not significant Signed and Sealed this Fourth Day of March 1986

[SEAL]

Attest:

DONALD J. QUIGG

Attesting Officer    Commissioner of Patents and Trademarks